United States Patent [19]

Weissmüller et al.

[11] Patent Number: 4,824,844
[45] Date of Patent: Apr. 25, 1989

[54] SACCHARINE SALTS OF SUBSTITUTED AMINES, FUNGICIDAL COMPOSITIONS AND USE

[75] Inventors: Joachim Weissmüller, Monheim; Paul Reinecke; Gerd Hänssler, both of Leverkusen, all of Fed. Rep. of Germany

[73] Assignee: Bayer Aktiengesellschaft, Leverkusen, Fed. Rep. of Germany

[21] Appl. No.: 118,109

[22] Filed: Nov. 5, 1987

[30] Foreign Application Priority Data

Nov. 22, 1986 [DE] Fed. Rep. of Germany ....... 3639900

[51] Int. Cl.$^4$ ............... A01N 43/80; A01N 43/84; C07D 417/02
[52] U.S. Cl. ............... 514/239.5; 514/212; 514/227.5; 514/238.8; 514/255; 514/321; 514/373; 540/484; 540/609; 544/59; 544/109; 544/135; 544/368; 546/198; 548/211
[58] Field of Search .......... 540/484, 609; 544/59, 544/109, 135, 368; 546/198; 548/211; 514/212, 222, 227, 238, 255, 321, 373, 238.8, 239.5

[56] References Cited

U.S. PATENT DOCUMENTS 4,241,058 12/1980 Pfiffner ........................ 544/178
4,495,184 1/1985 Knops et al. .................. 544/170

FOREIGN PATENT DOCUMENTS 3430805 9/1985 Fed. Rep. of Germany .

*Primary Examiner*—Robert W. Ramsuer
*Attorney, Agent, or Firm*—Sprung, Horn, Kramer & Woods

[57] ABSTRACT

Fungicidally active saccharine salts of substituted amines of the formula

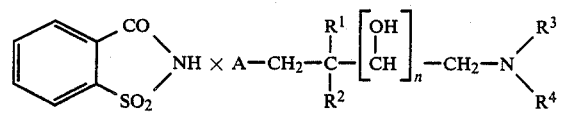

in which
A represents in each case optionally substituted cyclohexyl, cyclohexenyl or phenyl,
$R^1$ represents hydrogen or alkyl,
$R^2$ represents hydrogen or alkyl,
$R^3$ and $R^4$ independently of one another represent alkyl or, together with the nitrogen atom to which they are bonded, represent an optionally substituted saturated heterocyclic radical which can contain further hetero atoms and
n represents the number 0 or 1.

11 Claims, No Drawings

SACCHARINE SALTS OF SUBSTITUTED AMINES, FUNGICIDAL COMPOSITIONS AND USE

The invention relates to new saccharine salts of substituted amine, a process for their preparation and their use as agents for combating pests.

It is already known that saccharine salts of amines, such as, for example, the saccharine salt of 5-amino-1,2,4-triazole, have fungicidal properties (compare European Pat. No. 158,074).

It is furthermore known that certain substituted amines and salts thereof, such as, for example, the formic acid salt of 1-(4-t-butylphenyl)-3-(3,5-dimethyl-piperidin-1-yl)-2-methyl-propane, also have fungicidal properties (compare DE-OS (German Published Specification) No. 2,752,135).

However, the action of these already known compounds is not completely satisfactory in all fields of use when low amounts are applied and in the case of low concentrations.

New saccharine salts of substituted amines of the general formula (I)

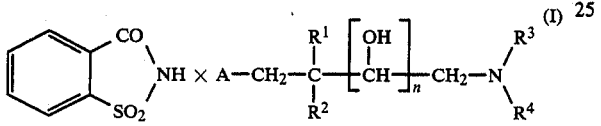

in which
- A represents in each case optionally substituted cyclohexyl, cyclohexenyl or phenyl,
- $R^1$ represents hydrogen or alkyl,
- $R^2$ represents hydrogen or alkyl,
- $R^3$ and $R^4$ independently of one another represent alkyl or, together with the nitrogen atom to which they are bonded, represent an optionally substituted saturated heterocyclic radical which can contain further hetero atoms and
- n represents the number 0 or 1, have been found.

The compounds of the formula (I) can exist as geometric and/or optical isomers or isomer mixtures of varying composition. Both the pure isomers and the isomer mixtures are claimed according to the invention.

It has furthermore been found that the new saccharine salts of substituted amines of the general formula (I)

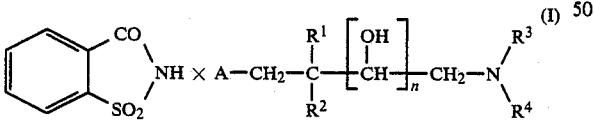

in which
- A represents in each case optionally substituted cyclohexyl, cyclohexenyl or phenyl,
- $R^1$ represents hydrogen or alkyl,
- $R^2$ represents hydrogen or alkyl,
- $R^3$ and $R^4$ independently of one another represent alkyl or, together with the nitrogen atom to which they are bonded, represent an optionally substituted saturated heterocyclic radical which can contain further hetero atoms and
- n represents the number 0 or 1, are obtained by a process in which substituted amines of the formula (II)

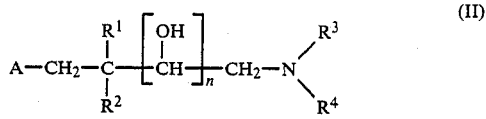

in which
- A, $R^1$, $R^2$, $R^3$, $R^4$ and n have the abovementioned meaning, are reacted with saccharine, if appropriate in the presence of a diluent.

Finally, it has been found that the new saccharine salts of substituted amines of the general formula (I) have an action against pests.

Surprisingly, the saccharine salts, according to the invention, of substituted amines of the general formula (I) inter alia have a better fungicidal activity than the saccharine salts, known from the prior art, of amines such as, for example, 5-amino-1,2,4-triazole, or the substituted amines known from the prior art and/or salts thereof, such as, for example, the formic acid salt of 1-(4-t-butyl-phenyl)-3-(3,5-dimethylpiperidin-1-yl)-2-methyl-propane, which are closely related compounds chemically and from the point of view of their action.

Formula (I) provides a general definition of the saccharine salts, according to the invention, of substituted amines. Preferred salts of the formula (I) are those in which
- A represents cyclohexyl or cyclohexenyl, in each case mono-, di- or trisubstituted by identical or different substituents, possible substituents in each case being: straight-chain or branched alkyl with 1 to 6 carbon atoms and halogenoalkyl and halogenoalkoxy with in each case 1 or 2 carbon atoms and 1 to 5 identical or different halogen atoms; or represents phenyl which is optionally mono-, di- or trisubstituted by identical or different substituents, possible substituents being: halogen, straight-chain or branched alkyl with 1 to 6 carbon atoms, halogenoalkyl and halogenoalkoxy with in each case 1 or 2 carbon atoms and 1 to 5 identical or different halogen atoms, alkenyl with 3 to 6 carbon atoms and cycloalkyl with 3 to 7 carbon atoms,
- $R^1$ represents hydrogen, or represents straight-chain or branched alkyl with 1 to 4 carbon atoms,
- $R^2$ represents hydrogen, or represents straight-chain or branched alkyl with 1 to 4 carbon atoms,
- $R^3$ and $R^4$ independently of one another in each case represent straight-chain or branched alkyl with 1 to 6 carbon atoms or, together with the nitrogen atom to which they are bonded, represent a saturated five- to seven-membered heterocyclic radical which is optionally mono-, di-, tri-, tetra- or pentasubstituted by identical or different substitutents and can contain, as further hetero atoms, in particular nitrogen, oxygen or sulphur, possible substituents being: hydroxyl and straight-chain or branched alkyl, hydroxyalkyl, acetoxyalkyl or propionyloxyalkyl with in each case 1 to 4 carbon atoms in the individual alkyl parts and
- n represents the number 0 or 1.

Particularly preferred salts of the formula (I) are those in which
- A represents cyclohexyl or cyclohexenyl, in each case mono- or disubstituted by identical or different substituents, substituents which may be mentioned in each case being: methyl, ethyl, n- or i-propyl, n-, i-, s-, t-butyl, 2-methyl-but-2-yl, trifluoromethyl and trifluoromethoxy; or represents phenyl which is optionally mono-, di- or trisubstituted by identical or different substituents, substituents which may be mentioned being: fluorine, chlorine, bromine, methyl, ethyl, n- or i-propyl, n-, i-, s- or t-butyl, 2-methyl-but-2-yl, trifluoromethyl, trifluoromethoxy, allyl, n- or i-butenyl and cyclohexyl;

$R^1$ represents hydrogen or methyl, $R^2$ represents hydrogen or methyl, $R^3$ and $R^4$ independently of one another in each case represent straight-chain or branched alkyl with in each case 1 to 6 carbon atoms or, together with the nitrogen atom to which they are bonded, represent a heterocyclic radical of the formula

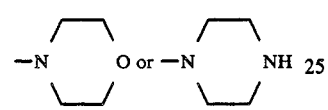

which is optionally mono-, di- or trisubstituted by identical or different substituents from the group comprising hydroxyl, hydroxymethyl, methyl, ethyl, acetoxymethyl and propionyloxymethyl and n represents the number 0 or 1.

Especially preferred salts are those of the formula (Ia)

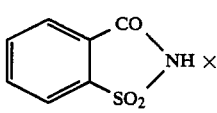
(Ia)

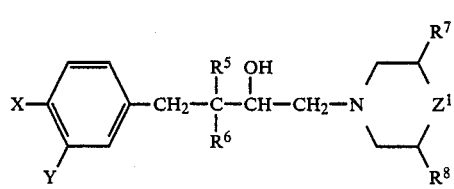

in which

X represents hydrogen, fluorine, chlorine, i-propyl or t-butyl,

Y represents hydrogen, fluorine, chlorine, methyl or ethyl, $R^5$ represents hydrogen or methyl, $R^6$ represents hydrogen or methyl, $R^7$ and $R^8$ in each case represent hydrogen, methyl or ethyl and $Z^1$ represents oxygen or a —CH$_2$— group.

Salts which are also especially preferred are those of the formula (Ib)

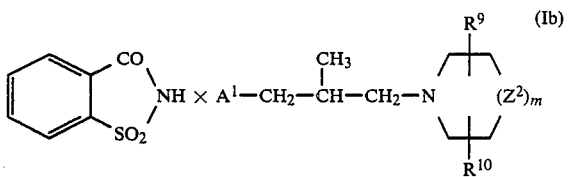

in which $A^1$ represents cyclohexyl or cyclohexenyl, in each case mono- or disubstituted by identical or different substituents, substituents which may be mentioned in each case being: methyl, ethyl, n- or i-propyl, n-, i-, s- or t-butyl and 2-methyl-but-2-yl; or represents phenyl which is mono- or disubstituted by identical or different substituents, substituents which may be mentioned being: fluorine, chlorine, bromine, methyl, ethyl, n- or i-propyl, n-, i-, s-, or t-butyl, 2-methyl-but-2-yl and cyclohexyl, $R^9$ and $R^{10}$ independently of one another represent hydrogen, methyl, ethyl, hydroxymethyl or acetoxymethyl, $Z^2$ represents oxygen, or represents a methylene or ethylene group which is optionally substituted by methyl or ethyl and m represents the number 0 or 1.

The following salts of the general formula (I) may be mentioned specifically:

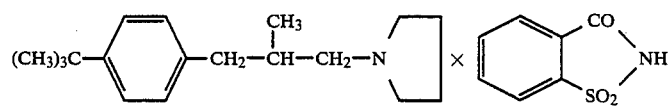

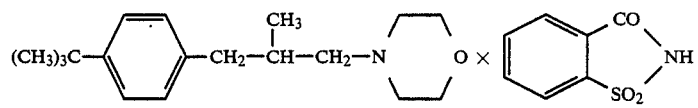

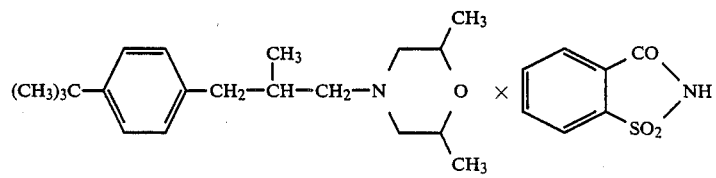

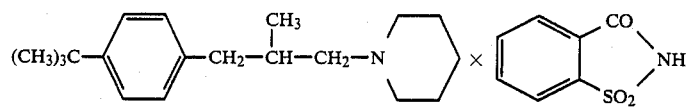
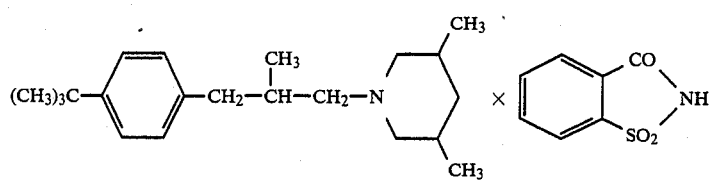
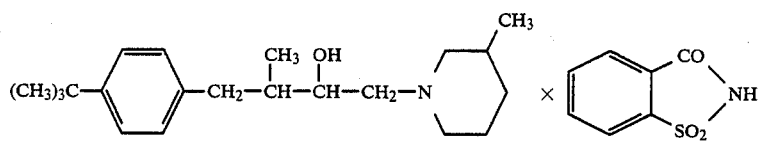
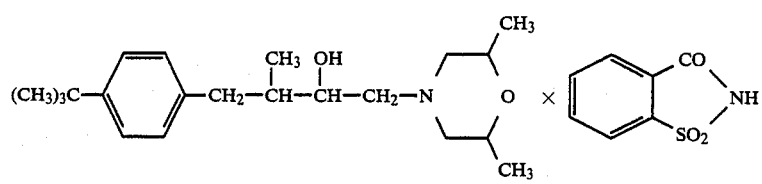
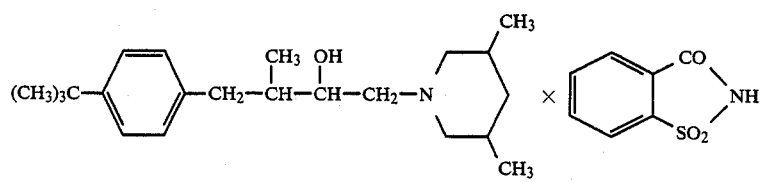
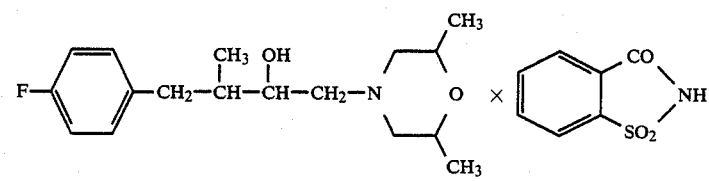
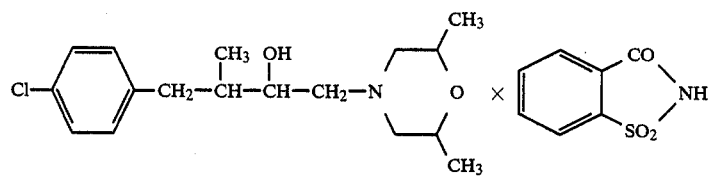
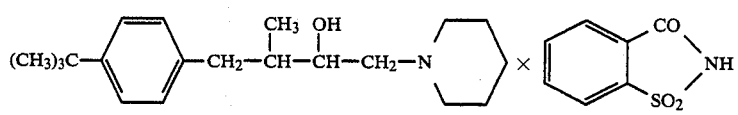
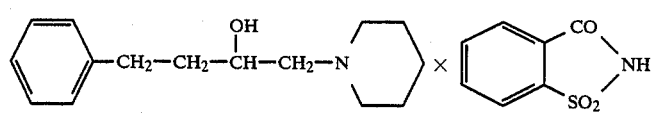
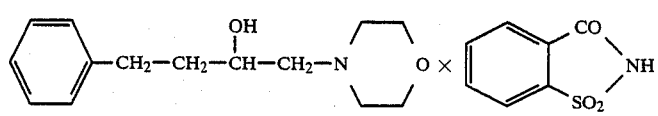

-continued
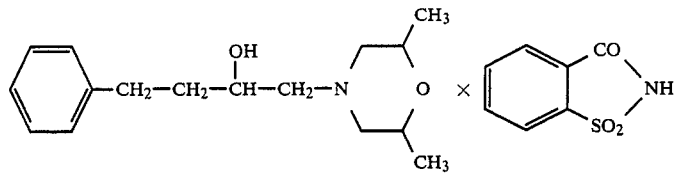
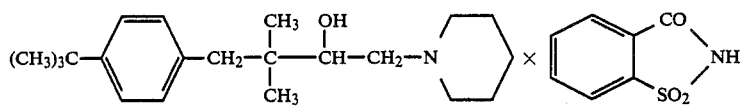
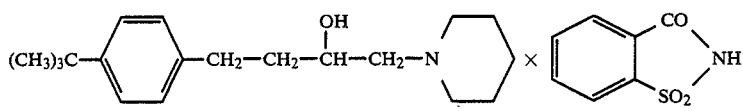
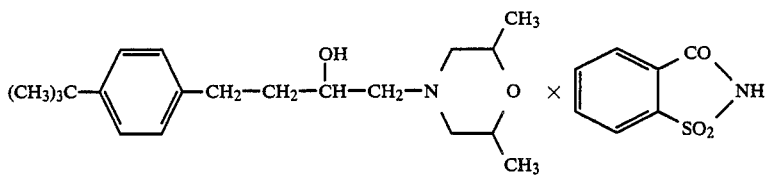
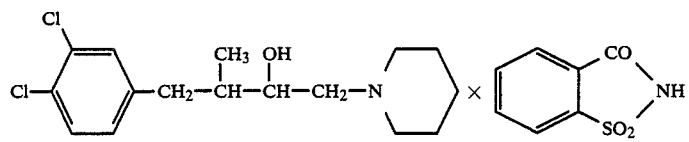
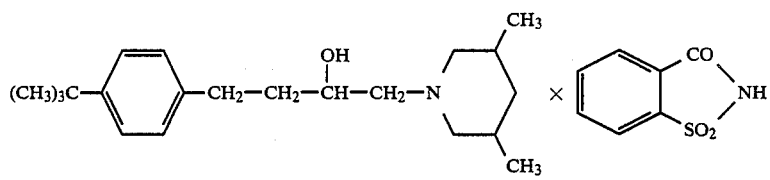
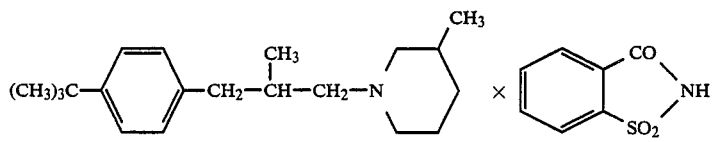
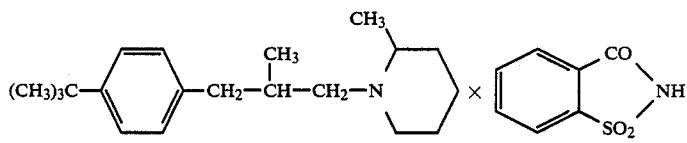
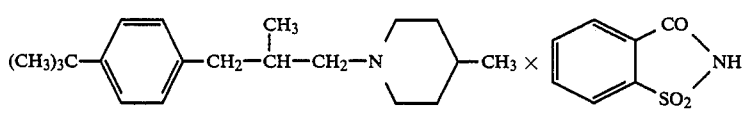
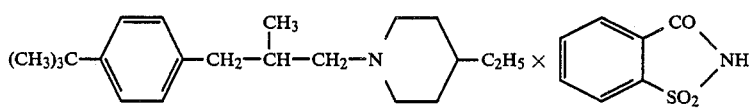
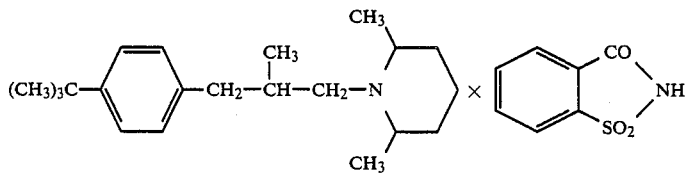

-continued
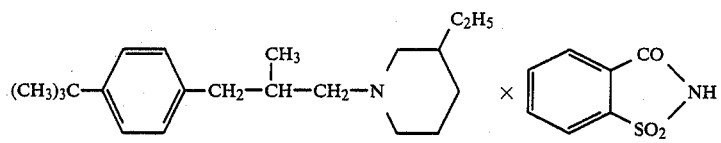
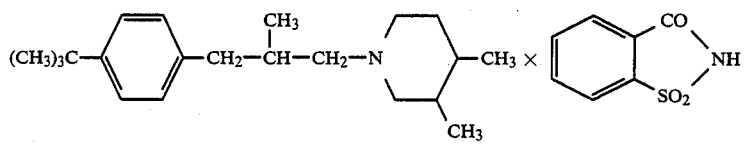
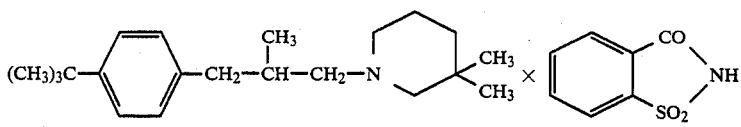
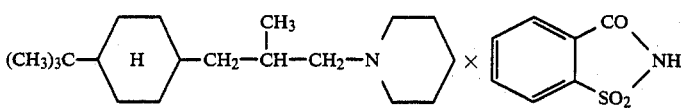
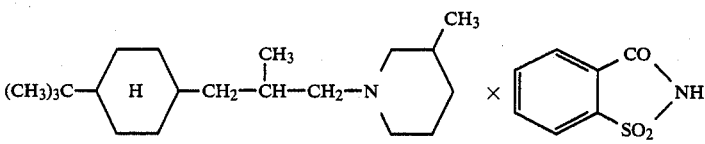
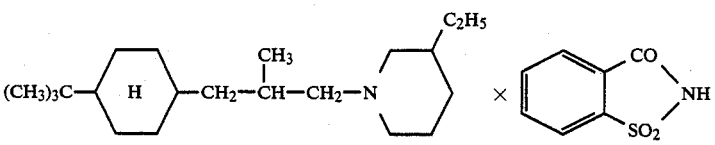
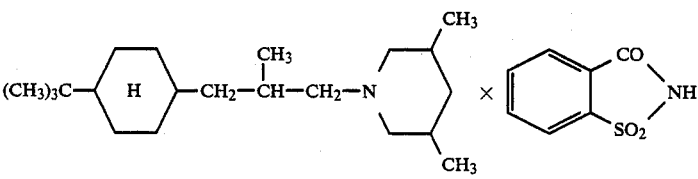
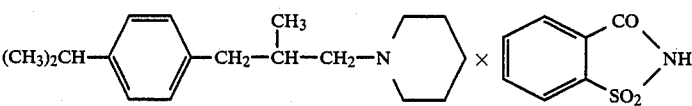
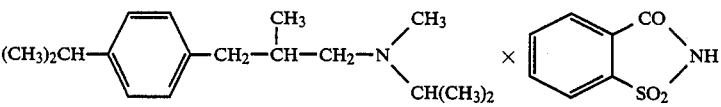
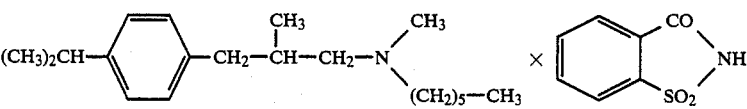
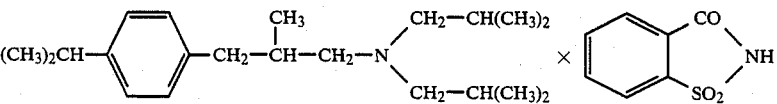

-continued
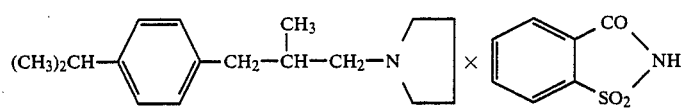
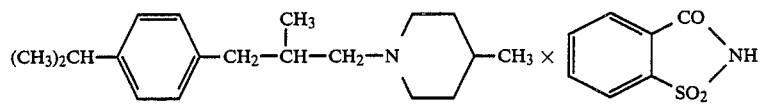
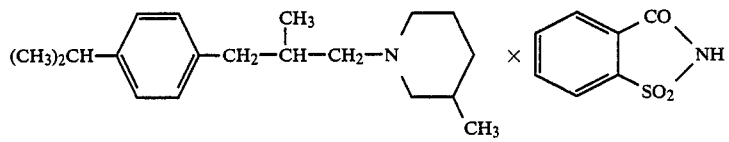
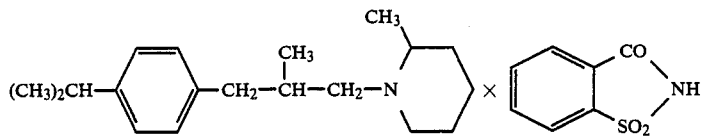
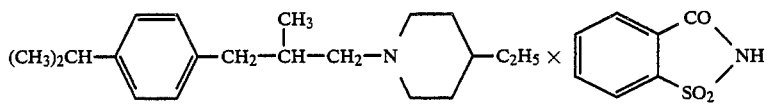
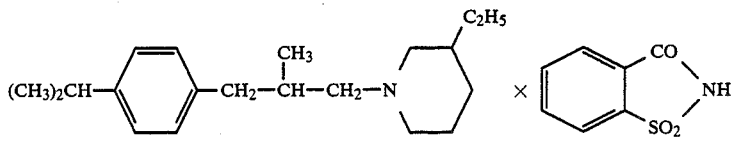
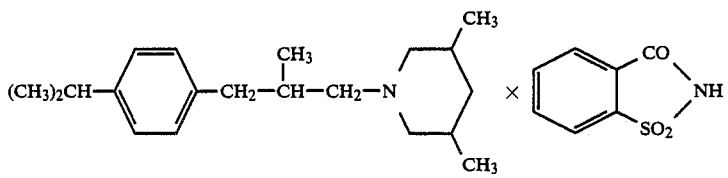
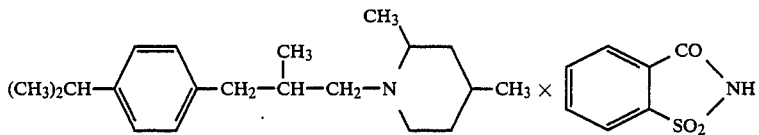
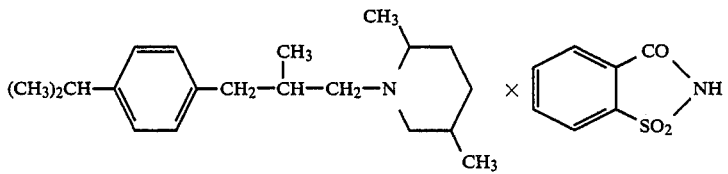
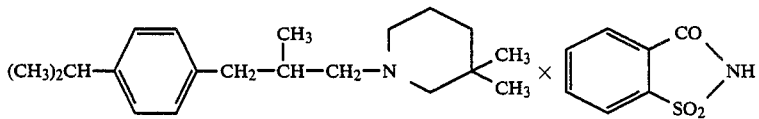
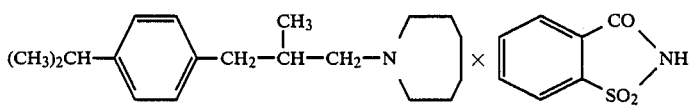

-continued
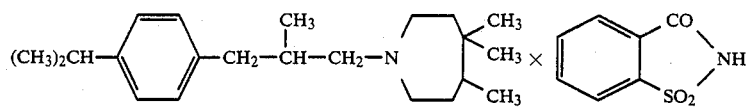
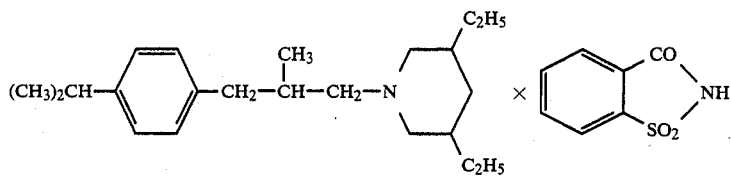
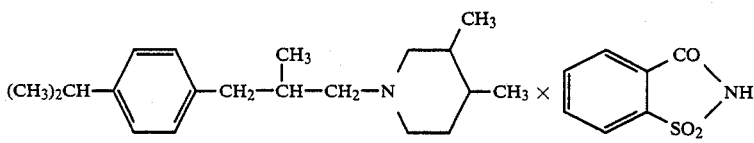
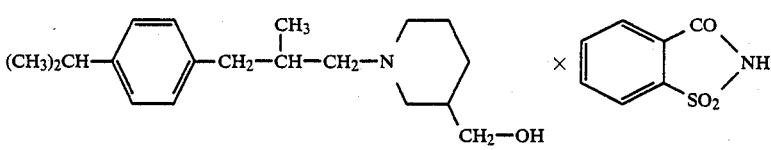
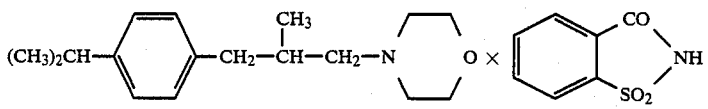
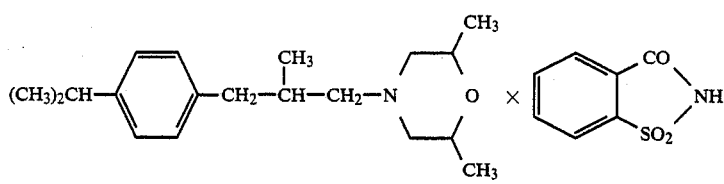
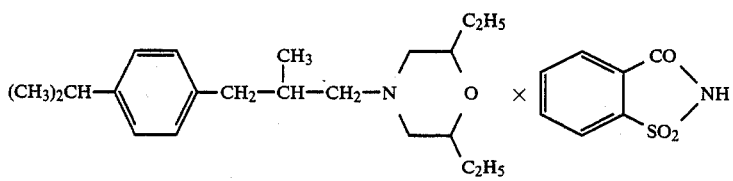
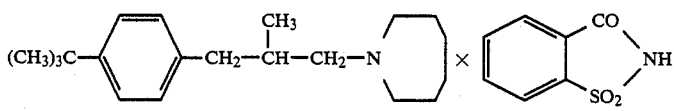
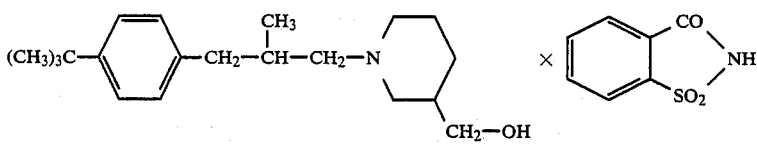
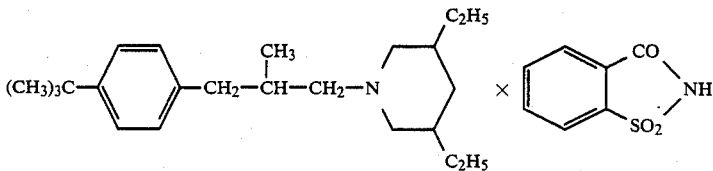

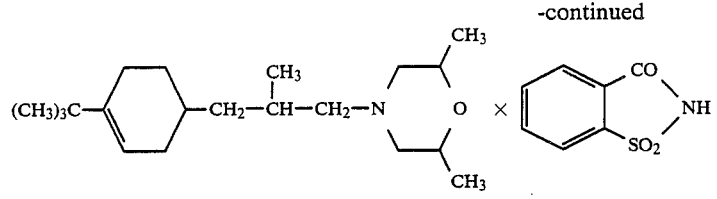

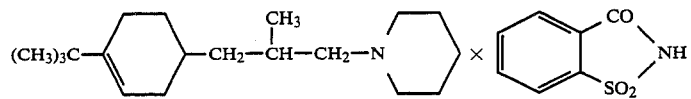

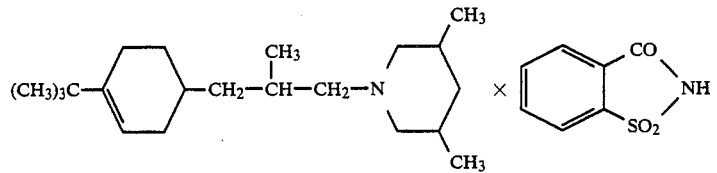

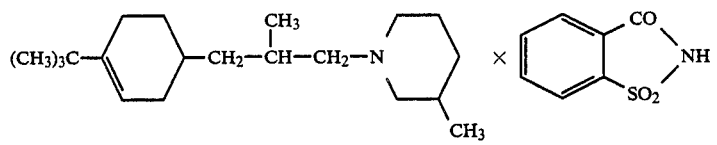

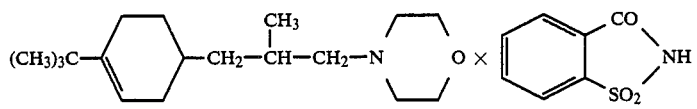

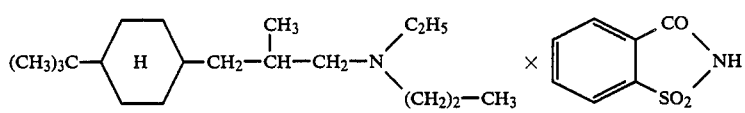

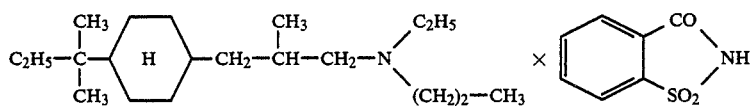

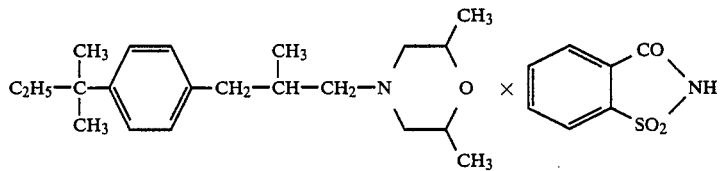

If, for example, 3-(2,6-dimethyl-4-morpholinyl)-2-methyl-1-(4-t-butyl-phenyl)-propane and saccharine are used as starting substances, the course of the reaction in the process according to the invention can be represented by the following equation:

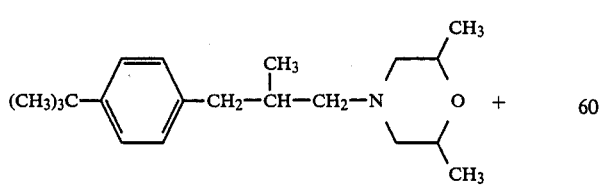

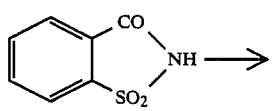

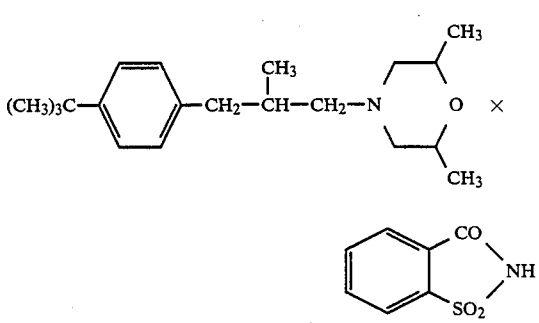

Formula (II) provides a general definition of the substituted amines required as starting substances for carrying out the process according to the invention. In this formula (II), A, $R^1$, $R^2$, $R^3$, $R^4$ and n represent those radicals which have already been mentioned for these substituents in connection with the description of the substances of the formula (I) according to the invention.

The substituted amines of the formula (II) are known (compare DE-OS (German Published Specification) No. 2,727,482, DE-OS (German Published Specification) No. 2,752,135, DE-OS (German Published Specification) No. 2,825,961, DE-OS (German Published Specification) No. 2,830,127, DE-OS (German Published Specification) No. 2,921,131, DE-OS (German Published Specification) No. 3,121,349, European Pat. No. 123,092 and European Pat. No. 129,321).

Possible diluents for carrying out the process according to the invention are inert organic solvents.

These include, in particular, ethers, such as diethyl ether, dioxane, tetrahydrofuran or ethylene glycol dimethyl or diethyl ether; ketones, such as acetone or butanone; nitriles, such as acetonitrile or propionitrile; amides, such as dimethylformamide, dimethylacetamide, N-methylformanilide, N-methylpyrrolidone or hexamethylphosphoric acid triamide, or alcohols, such as methanol, ethanol or propanol.

The reaction temperatures can be varied within a substantial range in carrying out the process according to the invention. The reaction is in general carried out at temperatures between 0° C. and 100° C., preferably at temperatures between 10° C. and 50° C.

For carrying out the process according to the invention, equimolar amounts of saccharine are added per mole of substituted amine of the formula (II). The two reaction partners are dissolved in a suitable solvent at the suitable reaction temperature and the solvent is then removed by distillation in vacuo. The salts thus obtainable, which are occasionally obtained as viscous oils or in amorphous form, can be purified by generally customary processes, such as, for example, by recrystallization or digestion in suitable solvents. They are characterized in these cases with the aid of spectroscopic methods (IR; NMR).

The active compounds according to the invention have a powerful action against pests and can be used in practice for combating undesirable harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can thereby be used with particularly good success for combating cereal diseases, such as, for example, against the powdery mildew of cereal causative organism (*Erysiphe graminis*), against the leaf spot disease causative organism (*Pyrenophora teres*), against Cercospora species and Botrytis species and against the rice spot disease causative organism (*Pyricularia oryzae*). It should be emphasized that as well as having a good protective activity, the active compounds according to the invention also have systemic properties. The active compounds according to the invention are moreover distinguished by a broad in vitro activity.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom by further dilution, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Preparation Examples

EXAMPLE 1

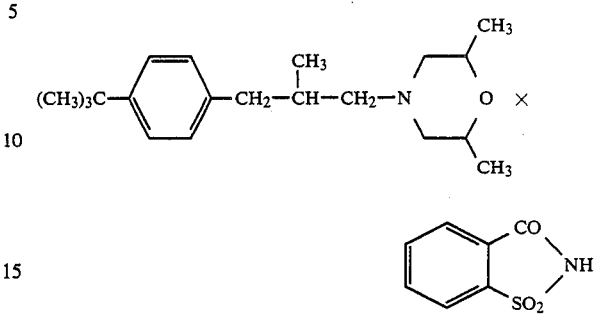

A solution of 3.6 g (0.02 mol) of saccharine in 50 ml of acetone is added to 6.4 g (0.02 mol) of 3-(4-t-butyl-phenyl)-2-methyl-1-(2,6-dimethyl-morpholin-4-yl)-propane in 50 ml of acetone and the mixture is stirred at room temperature for 45 minutes. The solvent is distilled off in vacuo and the residue is dried under a high vacuum.

10 g (100% of theory) of 3-(4-t-butyl-phenyl)-2-methyl-1-(2,6-dimethyl-morpholin-4-yl)-propane saccharine salt are obtained as a viscous oil solidified in vitreous form.

$^1$H-NMR (CDCl$_3$/tetramethylsilane): $\delta$=7.79 (m, 2H); 7.59 (m, 2H); 4.07 (m, 2H); 3.31 (dd, 2H); 1.1 (d. 3H) ppm.

The following compounds are obtained in a corresponding manner:

EXAMPLE 2

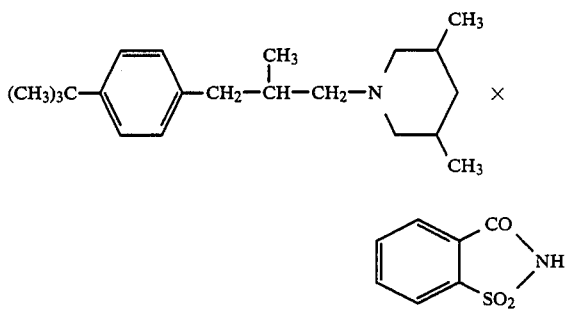

$^1$H-NMR (CDCl$_3$/TMS): $\delta$=3.5–3.6 (m, 2H); 2.6 (m, 2H) ppm.

EXAMPLE 3

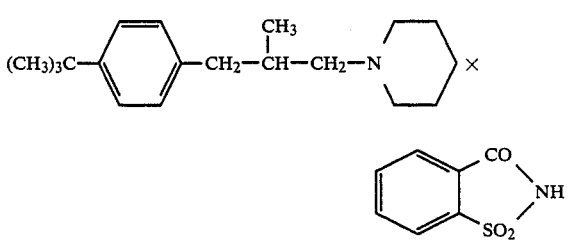

$^1$H-NMR (CDCl$_3$/TMS): $\delta$=3.6–3.8 (m, 2H); 2.9–3.1 (m), 1.13 (d, 3H) ppm.

EXAMPLE 4

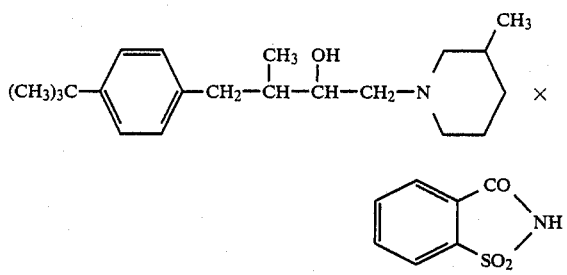

Melting point: 47°–52° C.

EXAMPLE 5

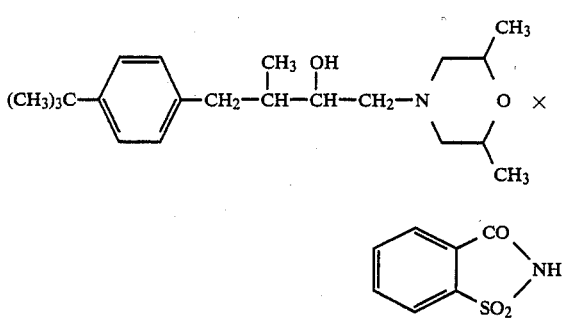

Melting point: 34°–38° C.

Use Examples

The compounds shown below were employed as comparison substances in the following use examples:

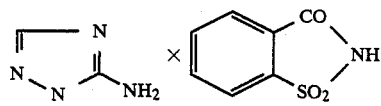
(A)

Saccharine salt of 5-amino-1,2,4-triazole (known from European Pat. No. 158,074) and

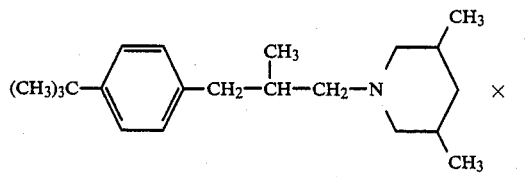
(B)

Formic acid salt of 1-(4-t-butylphenyl)-3-(3,5-dimethyl-piperidin-1-yl)-2-methyl-propane. (known from DE-OS (German Published Specification) No. 2,752,135).

EXAMPLE A

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. *hordei*.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the preparation Examples 1, 2 and 3.

EXAMPLE B

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the preparation Examples 1, 2 and 3.

It is understood that the specification and examples are illustrative but not limitative of the present invention and that other embodiments within the spirit and scope of the invention will suggest themselves to those skilled in the art.

We claim:

1. A saccharine salt of a substituted amine of the formula

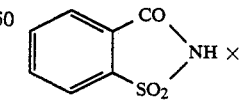

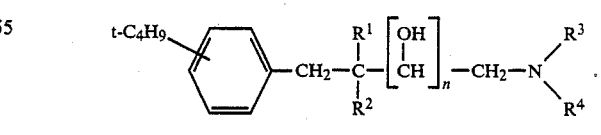

in which
$R^1$ represents hydrogen or alkyl,
$R^2$ represents alkyl,
$R^3$ and $R^4$ together with the nitrogen atom to which they are bonded, represent piperidine or morpholine unsubstituted or substituted by 1 or 2 lower alkyl radicals and
n represents the number 0 or 1.

2. A saccharine salt according to claim 1, in which

R$^1$ represents hydrogen, or represents straight-chain or branched alkyl with 1 to 4 carbon atoms, and R$^2$ represents represents straight-chain or branched alkyl with 1 to 4 carbon atoms.

3. A saccharine salt according to claim 1, in which

R$^1$ represents hydrogen or methyl, and

R$^2$ represents methyl.

4. A saccharine salt according to claim 1, of the formula

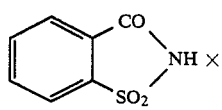

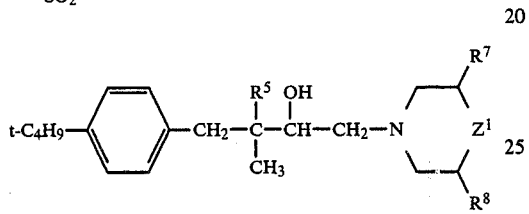

in which

R$^5$ represents hydrogen or methyl,

R$^7$ and R$^8$ in each case represent hydrogen, methyl or ethyl and

Z$^1$ represents oxygen or a —CH$_2$— group.

5. A saccharine salt according to claim 1, of the formula

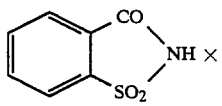

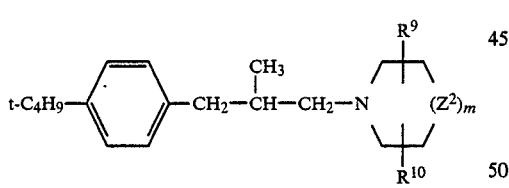

in which

R$^9$ and R$^{10}$ independently of one another represent methyl or ethyl,

Z$^2$ represents a methylene group and m represents the number 1.

6. A saccharine salt according to claim 1, wherein such salt is 3-(4-t-butyl-phenyl)-2-methyl-1-(2,6-dimethylmorpholin-4-yl)-propane saccharine salt of the formula

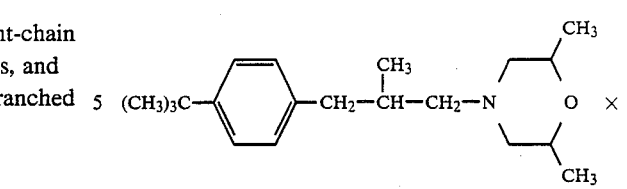

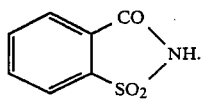

7. A saccharine salt according to claim 1, wherein such salt is 3-(4-t-butyl-phenyl)-2-methyl-1-(3,5-dimethylpiperidin-1-yl)-propane saccharine salt of the formula

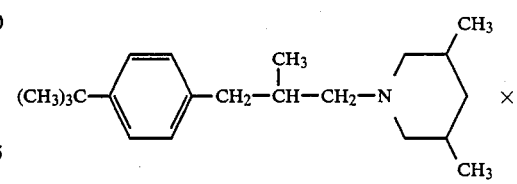

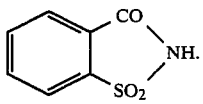

8. A saccharine salt according to claim 1, wherein such salt is 3-(4-t-butyl-phenyl-2-methyl-1-(piperidin-1-yl)-propane saccharine salt of the formula

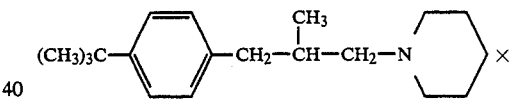

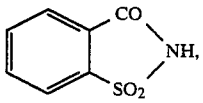

9. A fungicidal composition comprising a fungicidally effective amount of a saccharine salt according to claim 1 and a diluent.

10. A method of combating fungi which comprises ing to such fungi or to a fungus habitat a fungicidally effective amount of a saccharine salt according to claim 1.

11. The method according to claim 10 wherein such saccharine salt is the saccharine salt of
3-(4-t-butyl-phenyl)-2-methyl-1-(2,6-dimethylmorpholin-4-yl)-propane,
3-(4-t-butyl-phenyl)-2-methyl-1-(3,5-dimethylpiperidin-1-yl)-propane or
3-(4-t-butyl-phenyl-2-methyl-1-(piperidin-1-yl)-propane.

* * * * *